United States Patent
Altarac et al.

(10) Patent No.: US 8,945,183 B2
(45) Date of Patent: Feb. 3, 2015

(54) INTERSPINOUS PROCESS SPACER INSTRUMENT SYSTEM WITH DEPLOYMENT INDICATOR

(75) Inventors: Moti Altarac, Irvine, CA (US); Shawn Tebbe, Yorba Linda, CA (US); Daniel H. Kim, Houston, TX (US)

(73) Assignee: VertiFlex, Inc., San Clemente, CA (US)

( * ) Notice: Subject to any disclaimer, the term of this patent is extended or adjusted under 35 U.S.C. 154(b) by 734 days.

(21) Appl. No.: 12/400,601

(22) Filed: Mar. 9, 2009

(65) Prior Publication Data
US 2009/0222043 A1 Sep. 3, 2009

Related U.S. Application Data

(63) Continuation-in-part of application No. 12/354,517, filed on Jan. 15, 2009, which is a continuation-in-part of application No. 12/338,793, filed on Dec. 18, 2008, now Pat. No. 8,613,747, application No. 12/400,601,
(Continued)

(51) Int. Cl.
*A61F 2/44* (2006.01)
*A61B 17/70* (2006.01)
(Continued)

(52) U.S. Cl.
CPC ........... *A61B 17/7065* (2013.01); *A61B 17/861* (2013.01); *A61B 17/8877* (2013.01); *A61B 17/8888* (2013.01); *A61B 17/7062* (2013.01)
USPC ........................................ 606/249; 623/17.11

(58) Field of Classification Search
CPC ........... A61B 17/7062; A61B 17/7064; A61B 17/7065; A61B 17/7067; A61B 17/7068; A61F 2/4405; A61F 2/4441
USPC .................... 623/17.11–17.16; 606/247–253; 600/309, 505
See application file for complete search history.

(56) References Cited

U.S. PATENT DOCUMENTS 2,248,054 A  7/1941  Becker
2,677,369 A  5/1954  Knowles
(Continued)

FOREIGN PATENT DOCUMENTS

DE  69507480 T2  9/1999
EP     322334 B1  2/1992
(Continued)

OTHER PUBLICATIONS

International Search Report and Written Opinion for application No. PCT/US09/031710, Mail Date Sep. 1, 2009, 10 pages.
(Continued)

*Primary Examiner* — Christopher D Prone
(74) *Attorney, Agent, or Firm* — Perkins Coie LLP

(57) ABSTRACT

A percutaneous and minimally invasive instrument system for implanting an interspinous process spacer into a patient is disclosed. The insertion instrument system includes an inserter and a driver. The inserter is configured to releasably clamp to an interspinous process spacer for its delivery, implantation and deployment. The driver is configured for removable insertion into a proximal end of a passageway of the inserter. The driver has a distal spacer engaging portion configured to engage that part of the spacer requiring activation for the deployment of the spacer from at least one undeployed configuration to at least one deployed configuration and vice versa. As the spacer goes from the undeployed to the deployed configuration and vice versa, the system advantageously provides a degree of deployment information to the user via at least one deployment indicator.

20 Claims, 8 Drawing Sheets

Related U.S. Application Data which is a continuation-in-part of application No. 12/205,511, filed on Sep. 5, 2008, now Pat. No. 8,123,782, application No. 12/400,601, which is a continuation-in-part of application No. 12/220,427, filed on Jul. 24, 2008, now Pat. No. 8,277,488, application No. 12/400,601, which is a continuation-in-part of application No. 12/217,662, filed on Jul. 8, 2008, now Pat. No. 8,273,108, application No. 12/400,601, which is a continuation-in-part of application No. 12/148,104, filed on Apr. 16, 2008, now Pat. No. 8,292,922, application No. 12/400,601, which is a continuation-in-part of application No. 11/593,995, filed on Nov. 7, 2006, now Pat. No. 8,425,559, and a continuation-in-part of application No. 11/582,874, filed on Oct. 18, 2006, now Pat. No. 8,128,662, and a continuation-in-part of application No. 11/314,712, filed on Dec. 20, 2005, now Pat. No. 8,152,837, and a continuation-in-part of application No. 11/190,496, filed on Jul. 26, 2005, now Pat. No. 8,409,282, and a continuation-in-part of application No. 11/079,006, filed on Mar. 10, 2005, now Pat. No. 8,012,207, and a continuation-in-part of application No. 11/052,002, filed on Feb. 4, 2005, now Pat. No. 8,317,864, and a continuation-in-part of application No. 11/006,502, filed on Dec. 6, 2004, now Pat. No. 8,123,807, and a continuation-in-part of application No. 10/970,843, filed on Oct. 20, 2004, now Pat. No. 8,167,944, and a continuation-in-part of application No. 11/006,521, filed on Dec. 6, 2004, and a continuation-in-part of application No. 11/305,820, filed on Dec. 15, 2005, now Pat. No. 7,763,074.

(60) Provisional application No. 61/069,083, filed on Mar. 12, 2008, provisional application No. 61/011,199, filed on Jan. 15, 2008, provisional application No. 61/008,418, filed on Dec. 19, 2007, provisional application No. 60/967,805, filed on Sep. 7, 2007, provisional application No. 60/961,741, filed on Jul. 24, 2007, provisional application No. 60/958,876, filed on Jul. 9, 2007, provisional application No. 60/923,971, filed on Apr. 17, 2007, provisional application No. 60/923,841, filed on Apr. 16, 2007.

(51) Int. Cl.
*A61B 17/86* (2006.01)
*A61B 17/88* (2006.01)

(56) References Cited

U.S. PATENT DOCUMENTS

| | | | |
|---|---|---|---|
| 3,242,120 A | 3/1966 | Steuber | |
| 3,648,691 A | 3/1972 | Lumb et al. | |
| 3,986,383 A | 10/1976 | Petteys | |
| 4,632,101 A | 12/1986 | Freedland | |
| 4,685,447 A | 8/1987 | Iversen et al. | |
| 4,863,476 A * | 9/1989 | Shepperd | 623/17.15 |
| 4,895,564 A | 1/1990 | Farrell | |
| 5,011,484 A | 4/1991 | Breard | |
| 5,015,247 A | 5/1991 | Michelson | |
| 5,019,081 A | 5/1991 | Watanabe | |
| 5,059,193 A | 10/1991 | Kuslich | |
| 5,092,866 A | 3/1992 | Breard et al. | |
| 5,180,393 A | 1/1993 | Commarmond | |
| 5,182,281 A | 1/1993 | Frigola-Constansa et al. | |
| 5,188,281 A | 2/1993 | Fujiwara et al. | |
| 5,192,281 A | 3/1993 | de la Caffiniere | |
| 5,195,526 A | 3/1993 | Michelson | |
| 5,298,253 A | 3/1994 | LeFiles et al. | |
| 5,368,594 A | 11/1994 | Martin et al. | |
| 5,390,683 A | 2/1995 | Pisharodi | |
| 5,415,661 A | 5/1995 | Holmes | |
| 5,456,722 A | 10/1995 | McLeod et al. | |
| 5,462,738 A | 10/1995 | LeFiles et al. | |
| 5,472,452 A | 12/1995 | Trott | |
| 5,484,437 A | 1/1996 | Michelson | |
| 5,487,739 A | 1/1996 | Aebischer et al. | |
| 5,489,308 A | 2/1996 | Kuslich et al. | |
| 5,496,318 A | 3/1996 | Howland et al. | |
| 5,531,748 A | 7/1996 | de la Caffiniere | |
| 5,549,679 A | 8/1996 | Kuslich | |
| 5,571,189 A | 11/1996 | Kuslich | |
| 5,591,165 A | 1/1997 | Jackson | |
| 5,609,634 A | 3/1997 | Voydeville | |
| 5,609,636 A | 3/1997 | Kohrs et al. | |
| 5,645,599 A | 7/1997 | Samani | |
| 5,654,599 A | 8/1997 | Casper | |
| 5,658,337 A | 8/1997 | Kohrs et al. | |
| 5,674,295 A | 10/1997 | Ray et al. | |
| 5,700,264 A | 12/1997 | Zucherman et al. | |
| 5,725,582 A | 3/1998 | Bevan et al. | |
| 5,741,253 A | 4/1998 | Michelson | |
| 5,762,629 A | 6/1998 | Kambin | |
| 5,836,948 A | 11/1998 | Zucherman et al. | |
| 5,860,977 A | 1/1999 | Zucherman et al. | |
| 5,863,948 A | 1/1999 | Epstein et al. | |
| 5,876,404 A | 3/1999 | Zucherman et al. | |
| RE36,211 E | 5/1999 | Nonomura | |
| 5,904,636 A | 5/1999 | Chen et al. | |
| 5,904,686 A | 5/1999 | Zucherman et al. | |
| 5,972,015 A | 10/1999 | Scribner et al. | |
| 6,039,761 A | 3/2000 | Li et al. | |
| 6,045,552 A | 4/2000 | Zucherman et al. | |
| 6,048,342 A | 4/2000 | Zucherman et al. | |
| 6,066,154 A | 5/2000 | Reiley et al. | |
| 6,068,630 A | 5/2000 | Zucherman et al. | |
| 6,074,390 A | 6/2000 | Zucherman et al. | |
| 6,080,155 A | 6/2000 | Michelson | |
| 6,080,157 A | 6/2000 | Cathro et al. | |
| 6,090,112 A | 7/2000 | Zucherman et al. | |
| 6,096,038 A | 8/2000 | Michelson | |
| 6,102,928 A | 8/2000 | Bonutti | |
| D433,193 S | 10/2000 | Gaw et al. | |
| 6,132,464 A | 10/2000 | Martin et al. | |
| 6,149,642 A | 11/2000 | Gerhart et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,159,215 A | 12/2000 | Urbahns et al. | |
| 6,179,873 B1 | 1/2001 | Zientek | |
| 6,183,471 B1 | 2/2001 | Zucherman et al. | |
| 6,190,387 B1 | 2/2001 | Zucherman et al. | |
| 6,225,048 B1 | 5/2001 | Soderberg-Naucler et al. | |
| 6,235,030 B1 | 5/2001 | Zucherman et al. | |
| 6,238,397 B1 | 5/2001 | Zucherman et al. | |
| 6,264,651 B1 | 7/2001 | Underwood et al. | |
| 6,264,656 B1 | 7/2001 | Michelson | |
| 6,267,765 B1 | 7/2001 | Taylor et al. | |
| 6,270,498 B1 | 8/2001 | Michelson | |
| 6,280,444 B1 | 8/2001 | Zucherman et al. | |
| 6,312,431 B1 | 11/2001 | Asfora | |
| 6,332,882 B1 | 12/2001 | Zucherman et al. | |
| 6,332,883 B1 | 12/2001 | Zucherman et al. | |
| 6,336,930 B1 | 1/2002 | Stalcup et al. | |
| 6,348,053 B1 | 2/2002 | Cachia | |
| 6,364,883 B1 | 4/2002 | Santilli | |
| 6,371,989 B1 | 4/2002 | Chauvin et al. | |
| 6,375,682 B1 | 4/2002 | Fleischmann et al. | |
| 6,379,355 B1 | 4/2002 | Zucherman et al. | |
| 6,395,032 B1 | 5/2002 | Gauchet et al | |
| 6,402,740 B1 | 6/2002 | Ellis et al. | |
| 6,402,750 B1 | 6/2002 | Atkinson et al. | |
| 6,402,784 B1 | 6/2002 | Wardlaw et al. | |
| 6,413,228 B1 | 7/2002 | Hung et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,443,988 B2 | 9/2002 | Felt et al. | |

(56) References Cited

U.S. PATENT DOCUMENTS

| | | |
|---|---|---|
| 6,447,547 B1 | 9/2002 | Michelson |
| 6,451,019 B1 | 9/2002 | Zucherman et al. |
| 6,451,020 B1 | 9/2002 | Zucherman et al. |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas |
| 6,575,981 B1 | 6/2003 | Boyd et al. |
| 6,579,319 B2 | 6/2003 | Goble et al. |
| 6,582,433 B2 | 6/2003 | Yun |
| 6,582,451 B1 | 6/2003 | Marucci et al. |
| 6,610,065 B1 | 8/2003 | Branch et al. |
| 6,610,091 B1 | 8/2003 | Reiley |
| 6,626,944 B1 | 9/2003 | Taylor |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 * | 3/2004 | DiCarlo .................. 623/1.34 |
| 6,712,819 B2 | 3/2004 | Zucherman et al. |
| 6,716,245 B2 | 4/2004 | Pasquet et al. |
| 6,733,534 B2 | 5/2004 | Sherman |
| 6,746,485 B1 | 6/2004 | Zucherman et al. |
| 6,761,720 B1 | 7/2004 | Senegas |
| 6,783,529 B2 | 8/2004 | Hover et al. |
| 6,796,983 B1 | 9/2004 | Zucherman et al. |
| 6,835,205 B2 | 12/2004 | Atkinson et al. |
| 6,858,029 B2 | 2/2005 | Yeh et al. |
| 6,869,398 B2 | 3/2005 | Obenchain et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Amin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,252,673 B2 | 8/2007 | Lim |
| 7,273,496 B2 | 9/2007 | Mitchell |
| 7,282,063 B2 | 10/2007 | Cohen et al. |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,410,501 B2 | 8/2008 | Michelson |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,520,899 B2 | 4/2009 | Zucherman et al. |
| 7,547,308 B2 | 6/2009 | Bertagnoli et al. |
| 7,550,009 B2 | 6/2009 | Amin et al. |
| 7,572,276 B2 | 8/2009 | Lim et al. |
| 7,575,600 B2 | 8/2009 | Zucherman et al. |
| 7,591,851 B2 | 9/2009 | Winslow et al. |
| 7,601,170 B2 | 10/2009 | Winslow et al. |
| 7,635,378 B2 | 12/2009 | Zucherman et al. |
| 7,637,950 B2 | 12/2009 | Baccelli et al. |
| 7,662,187 B2 | 2/2010 | Zucherman et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,699,852 B2 | 4/2010 | Frankel et al. |
| 7,758,619 B2 | 7/2010 | Zucherman et al. |
| 7,763,050 B2 | 7/2010 | Winslow et al. |
| 7,776,090 B2 | 8/2010 | Winslow et al. |
| 7,789,898 B2 | 9/2010 | Peterman |
| 7,837,711 B2 | 11/2010 | Bruneau et al. |
| 7,837,734 B2 | 11/2010 | Zucherman et al. |
| 7,846,183 B2 | 12/2010 | Blain |
| 7,857,815 B2 | 12/2010 | Zucherman et al. |
| 7,862,569 B2 | 1/2011 | Zucherman et al. |
| 7,862,586 B2 | 1/2011 | Malek |
| 8,273,108 B2 | 9/2012 | Altarac et al. |
| 8,292,922 B2 | 10/2012 | Altarac et al. |
| 2001/0031965 A1 | 10/2001 | Zucherman et al. |
| 2002/0029083 A1 | 3/2002 | Zucherman et al. |
| 2002/0072752 A1 | 6/2002 | Zucherman et al. |
| 2002/0143331 A1 | 10/2002 | Zucherman et al. |
| 2003/0040746 A1 | 2/2003 | Mitchell et al. |
| 2003/0074075 A1 | 4/2003 | Thomas et al. |
| 2003/0135275 A1 * | 7/2003 | Garcia et al. ............... 623/17.11 |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2004/0006341 A1 | 1/2004 | Shaolian et al. |
| 2004/0087947 A1 | 5/2004 | Lim et al. |
| 2004/0106995 A1 | 6/2004 | Le Couedic et al. |
| 2004/0153065 A1 | 8/2004 | Lim |
| 2004/0162617 A1 | 8/2004 | Zucherman et al. |
| 2004/0167625 A1 | 8/2004 | Beyar et al. |
| 2004/0193159 A1 | 9/2004 | Zucherman et al. |
| 2004/0199255 A1 | 10/2004 | Mathieu et al. |
| 2004/0220568 A1 | 11/2004 | Zucherman et al. |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0033295 A1 | 2/2005 | Wisnewski |
| 2005/0049708 A1 | 3/2005 | Atkinson et al. |
| 2005/0075634 A1 | 4/2005 | Zucherman et al. |
| 2005/0085813 A1 | 4/2005 | Spitler et al. |
| 2005/0101955 A1 | 5/2005 | Zucherman et al. |
| 2005/0125063 A1 | 6/2005 | Matge et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0182416 A1 | 8/2005 | Lim et al. |
| 2005/0192586 A1 | 9/2005 | Zucherman et al. |
| 2005/0192671 A1 | 9/2005 | Bao et al. |
| 2005/0196420 A1 | 9/2005 | Zucherman et al. |
| 2005/0203512 A1 | 9/2005 | Hawkins et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0240182 A1 | 10/2005 | Zucherman et al. |
| 2005/0245937 A1 | 11/2005 | Winslow |
| 2005/0261768 A1 | 11/2005 | Trieu |
| 2005/0278028 A1 | 12/2005 | Mujwid |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |

(56) References Cited

U.S. PATENT DOCUMENTS

| | | |
|---|---|---|
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0190083 A1 | 8/2006 | Arnin et al. |
| 2006/0195102 A1 | 8/2006 | Malandain |
| 2006/0217726 A1 | 9/2006 | Maxy et al. |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0235387 A1 | 10/2006 | Peterman |
| 2006/0235521 A1 | 10/2006 | Zucherman et al. |
| 2006/0241610 A1 | 10/2006 | Lim et al. |
| 2006/0241613 A1 | 10/2006 | Bruneau et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247640 A1 | 11/2006 | Blackwell et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282075 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0293662 A1 | 12/2006 | Boyer, II et al. |
| 2007/0010813 A1 | 1/2007 | Zucherman et al. |
| 2007/0016196 A1 | 1/2007 | Winslow et al. |
| 2007/0032790 A1 | 2/2007 | Aschmann et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0073292 A1* | 3/2007 | Kohm et al. .................... 606/61 |
| 2007/0093830 A1 | 4/2007 | Zucherman et al. |
| 2007/0100340 A1 | 5/2007 | Lange et al. |
| 2007/0100366 A1 | 5/2007 | Dziedzic et al. |
| 2007/0106298 A1 | 5/2007 | Carli et al. |
| 2007/0106385 A1 | 5/2007 | Zucherman et al. |
| 2007/0118120 A1 | 5/2007 | Farris et al. |
| 2007/0123863 A1 | 5/2007 | Winslow et al. |
| 2007/0123904 A1 | 5/2007 | Stad et al. |
| 2007/0142915 A1 | 6/2007 | Altarac et al. |
| 2007/0161991 A1 | 7/2007 | Altarac et al. |
| 2007/0161992 A1 | 7/2007 | Kwak et al. |
| 2007/0161993 A1 | 7/2007 | Lowery et al. |
| 2007/0162005 A1 | 7/2007 | Peterson et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191834 A1 | 8/2007 | Bruneau et al. |
| 2007/0191847 A1 | 8/2007 | Arnin et al. |
| 2007/0191947 A1 | 8/2007 | Arnin et al. |
| 2007/0191948 A1 | 8/2007 | Arnin et al. |
| 2007/0191949 A1 | 8/2007 | Arnin et al. |
| 2007/0191950 A1 | 8/2007 | Arnin et al. |
| 2007/0198045 A1 | 8/2007 | Morton et al. |
| 2007/0198091 A1 | 8/2007 | Boyer et al. |
| 2007/0203490 A1 | 8/2007 | Zucherman et al. |
| 2007/0203493 A1 | 8/2007 | Zucherman et al. |
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208347 A1 | 9/2007 | Zucherman et al. |
| 2007/0208366 A1 | 9/2007 | Pellegrino et al. |
| 2007/0213724 A1 | 9/2007 | Arnin et al. |
| 2007/0213829 A1 | 9/2007 | Le Couedic et al. |
| 2007/0219552 A1 | 9/2007 | Zucherman et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0239279 A1 | 10/2007 | Francis |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270812 A1 | 11/2007 | Peckham |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |

(56) References Cited

U.S. PATENT DOCUMENTS

| | | |
|---|---|---|
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071378 A1 | 3/2008 | Zucherman et al. |
| 2008/0086212 A1 | 4/2008 | Zucherman et al. |
| 2008/0108990 A1* | 5/2008 | Mitchell et al. ............... 606/61 |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177272 A1 | 7/2008 | Zucherman et al. |
| 2008/0183210 A1 | 7/2008 | Zucherman et al. |
| 2008/0188895 A1 | 8/2008 | Cragg et al. |
| 2008/0188941 A1 | 8/2008 | Grotz |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0215094 A1 | 9/2008 | Taylor |
| 2008/0221692 A1 | 9/2008 | Zucherman et al. |
| 2008/0228225 A1 | 9/2008 | Trautwein et al. |
| 2008/0234824 A1 | 9/2008 | Youssef et al. |
| 2008/0287997 A1 | 11/2008 | Altarac et al. |
| 2008/0288075 A1 | 11/2008 | Zucherman et al. |
| 2008/0294263 A1 | 11/2008 | Altarac et al. |
| 2008/0319550 A1 | 12/2008 | Altarac et al. |
| 2009/0118833 A1 | 5/2009 | Hudgins et al. |
| 2009/0125030 A1 | 5/2009 | Tebbe et al. |
| 2009/0138046 A1 | 5/2009 | Altarac et al. |
| 2009/0138055 A1 | 5/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0262243 A1 | 10/2010 | Zucherman et al. |
| 2010/0305611 A1 | 12/2010 | Zucherman et al. |
| 2011/0313457 A1 | 12/2011 | Reglos et al. |

FOREIGN PATENT DOCUMENTS

| | | |
|---|---|---|
| EP | 767636 B1 | 1/1999 |
| EP | 768843 B1 | 2/1999 |
| EP | 1027004 | 8/2000 |
| EP | 1030615 | 8/2000 |
| EP | 1138268 A1 | 10/2001 |
| EP | 1330987 | 7/2003 |
| EP | 1056408 B1 | 12/2003 |
| EP | 1343424 B1 | 9/2004 |
| EP | 1148850 B1 | 4/2005 |
| EP | 1299042 B1 | 3/2006 |
| EP | 1578314 B1 | 5/2007 |
| EP | 1675535 B1 | 5/2007 |
| EP | 959792 B1 | 11/2007 |
| WO | 9404088 A1 | 3/1994 |
| WO | 9426192 A1 | 11/1994 |
| WO | 9525485 A1 | 9/1995 |
| WO | 9531158 A1 | 11/1995 |
| WO | 9600049 A1 | 1/1996 |
| WO | 9829047 A1 | 7/1998 |
| WO | 9921500 A1 | 5/1999 |
| WO | 9921501 C2 | 8/1999 |
| WO | 9942051 A1 | 8/1999 |
| WO | 0013619 | 3/2000 |
| WO | 0044319 A1 | 8/2000 |
| WO | 0044321 A2 | 12/2000 |
| WO | 0128442 A1 | 4/2001 |
| WO | 0191657 A1 | 12/2001 |
| WO | 0191658 A1 | 12/2001 |
| WO | 0203882 A2 | 1/2002 |
| WO | 0207623 A1 | 1/2002 |
| WO | 0207624 A1 | 1/2002 |
| WO | 02051326 A1 | 7/2002 |
| WO | 02071960 A1 | 9/2002 |
| WO | WO-02067793 A2 | 9/2002 |
| WO | WO-02076336 A2 | 10/2002 |
| WO | 03007791 A2 | 1/2003 |
| WO | 03007829 A1 | 1/2003 |
| WO | 03008016 A2 | 1/2003 |
| WO | 03015646 A2 | 2/2003 |
| WO | WO-03024298 A2 | 3/2003 |
| WO | 03045262 A2 | 6/2003 |
| WO | 03099147 A1 | 12/2003 |
| WO | 03101350 A1 | 12/2003 |
| WO | 03024298 C2 | 6/2004 |
| WO | 04073533 | 9/2004 |
| WO | WO-2004073533 A1 | 9/2004 |
| WO | 2004110300 A2 | 12/2004 |
| WO | 2005013839 A2 | 2/2005 |
| WO | WO-2005009300 A1 | 2/2005 |
| WO | 2005025461 A2 | 3/2005 |
| WO | 2005041799 A1 | 5/2005 |
| WO | 2005044152 A1 | 5/2005 |
| WO | 2005055868 A2 | 6/2005 |
| WO | 2005079672 A2 | 9/2005 |
| WO | 2005115261 A1 | 12/2005 |
| WO | 2006033659 A2 | 3/2006 |
| WO | 2006034423 A2 | 3/2006 |
| WO | 2006039260 A2 | 4/2006 |
| WO | WO-2006039243 | 4/2006 |
| WO | 2006045094 C2 | 6/2006 |
| WO | 2006063047A2 A2 | 6/2006 |
| WO | 2006065774 A1 | 6/2006 |
| WO | 2006102269 A2 | 9/2006 |
| WO | 2006102428 A1 | 9/2006 |
| WO | 2006102485 A2 | 9/2006 |
| WO | 2006107539 A1 | 10/2006 |
| WO | 2006110462 A2 | 10/2006 |
| WO | 2006110464 A1 | 10/2006 |
| WO | 2006110767 A1 | 10/2006 |
| WO | 2006113080 A2 | 10/2006 |
| WO | 2006113406 A2 | 10/2006 |
| WO | 2006113814 A2 | 10/2006 |
| WO | 2006119235 A1 | 11/2006 |
| WO | 2006119236 A2 | 11/2006 |
| WO | 2006118945 C1 | 12/2006 |
| WO | 2006135511 A1 | 12/2006 |
| WO | 2007015028 A1 | 2/2007 |
| WO | 2007035120 A1 | 3/2007 |
| WO | 2007075375 A2 | 7/2007 |
| WO | 2007075788 A2 | 7/2007 |
| WO | 2007075791 A2 | 7/2007 |
| WO | 2007089605 A2 | 8/2007 |
| WO | 2007089905 A2 | 8/2007 |
| WO | 2007089975 A2 | 8/2007 |
| WO | 2007097735 A2 | 8/2007 |
| WO | 2007109402 A2 | 9/2007 |
| WO | 2007110604 A1 | 10/2007 |
| WO | 2007111795 A1 | 10/2007 |
| WO | 2007111979 A2 | 10/2007 |
| WO | 2007111999 A2 | 10/2007 |
| WO | 2007117882 A1 | 10/2007 |

(56) References Cited

FOREIGN PATENT DOCUMENTS

| WO | 2007121070 A2 | 10/2007 |
| --- | --- | --- |
| WO | 2007127550 A2 | 11/2007 |
| WO | 2007127588 A1 | 11/2007 |
| WO | 2007127677 A1 | 11/2007 |
| WO | 2007127689 A2 | 11/2007 |
| WO | 2007127694 A2 | 11/2007 |
| WO | 2007127734 A2 | 11/2007 |
| WO | 2007127736 A2 | 11/2007 |
| WO | 2007131165 A2 | 11/2007 |
| WO | 2007134113 A2 | 11/2007 |
| WO | 2008048645 | 4/2008 |

OTHER PUBLICATIONS

International Search Report and Written Opinion for application No. PCT/US09/031150, Mail Date Aug. 28, 2009, 7 pages.

International Search Report and Written Opinion for application No. PCT/US09/036561, Mail Date Sep. 17, 2009, 12 pages.

Minns R.J. et al., "Preliminary Design and Experiment Studies of a Novel Soft Implant for Correcting Sagittal Plane Instability in the Lumbar Spine," Spine, 1997, 22(16), 1819-1827.

International Search Report and Written Opinion for application No. PCT/US2008/087527, Mail Date Jul. 30, 2009, 15 pages.

Final Office Action; U.S. Appl. No. 10/970,843; Mailing Date: Feb. 12, 2009, 7 pages.

Final Office Action; U.S. Appl. No. 10/970,843; Mailing Date: Jul. 2, 2010, 9 pages.

Final Office Action; U.S. Appl. No. 11/006,502; Mailing Date: Aug. 17, 2009, 7 pages.

Final Office Action; U.S. Appl. No. 11/006,521; Mailing Date: May 17, 2010, 10 pages.

Final Office Action; U.S. Appl. No. 11/006,521; Mailing Date: Dec. 5, 2008, 10 pages.

Final Office Action; U.S. Appl. No. 11/052,002; Mailing Date: Apr. 1, 2009, 7 pages.

Final Office Action; U.S. Appl. No. 11/052,002; Mailing Date: Sep. 1, 2010, 7 pages.

Final Office Action; U.S. Appl. No. 11/079,006; Mailing Date: Nov. 10, 2009, 7 pages.

Final Office Action; U.S. Appl. No. 11/190,496; Mailing Date: May 19, 2009, 8 pages.

Final Office Action; U.S. Appl. No. 11/305,820; Mailing Date: Jun. 16, 2008, 9 pages.

Final Office Action; U.S. Appl. No. 11/314,712; Mailing Date: Sep. 4, 2009, 9 pages.

Final Office Action; U.S. Appl. No. 11/582,874; Mailing Date: Sep. 10, 2010, 10 pages.

International Search Report and Written Opinion; Application No. PCT/US2005/038026; Mailing Date: Apr. 22, 2008, 9 pages.

International Search Report and Written Opinion; Application No. PCT/US2005/044256; Mailing Date: Jul. 28, 2006, 7 pages.

International Search Report and Written Opinion; Application No. PCT/US2006/047824; Mailing Date: Oct. 16, 2008, 3 pages.

International Search Report and Written Opinion; Application No. PCT/US2006/048611; Mailing Date: Oct. 14, 2008; 10 pages.

International Search Report and Written Opinion; Application No. PCT/US2006/048614; Mailing Date: Feb. 3, 2006; 23 pages.

International Search Report and Written Opinion; Application No. PCT/US2007/022171; Mailing Date: Apr. 15, 2008, 13 pages.

International Search Report and Written Opinion; Application No. PCT/US2007/023312; Mailing Date: May 22, 2008, 14 pages.

International Search Report and Written Opinion; Application No. PCT/US2008/004901; Mailing Date: Aug. 19, 2008, 7 pages.

International Search Report and Written Opinion; Application No. PCT/US2008/008382; Mailing Date: Mar. 2, 2009, 12 pages.

International Search Report and Written Opinion; Application No. PCT/US2008/008983; Mailing Date: Feb. 23, 2009, 7 pages.

International Search Report and Written Opinion; Application No. PCT/US2008/075487; Mailing Date: Dec. 31, 2008, 7 pages.

Non-Final Office Action; U.S. Appl. No. 10/970,843; Mailing Date: Aug. 29, 2008, 9 pages.

Non-Final Office Action; U.S. Appl. No. 10/970,843; Mailing Date: Oct. 8, 2009, 8 pages.

Non-Final Office Action; U.S. Appl. No. 11/006,502; Mailing Date: Nov. 7, 2008, 7 pages.

Non-Final Office Action; U.S. Appl. No. 11/006,521; Mailing Date: Feb. 28, 2008, 13 pages.

Non-Final Office Action; U.S. Appl. No. 11/006,521; Mailing Date: Aug. 26, 2009, 9 pages.

Non-Final Office Action; U.S. Appl. No. 11/052,002; Mailing Date: Sep. 18, 2007, 7 pages.

Non-Final Office Action; U.S. Appl. No. 11/052,002; Mailing Date: Dec. 24, 2009, 6 pages.

Non-Final Office Action; U.S. Appl. No. 11/079,006; Mailing Date: Jan. 30, 2009, 7 pages.

Non-Final Office Action; U.S. Appl. No. 11/079,006; Mailing Date: Sep. 18, 2007, 6 pages.

Non-Final Office Action; U.S. Appl. No. 11/190,496; Mailing Date: Aug. 25, 2008, 6 pages.

Non-Final Office Action; U.S. Appl. No. 11/190,496; Mailing Date: Oct. 31, 2007, 7 pages.

Non-Final Office Action; U.S. Appl. No. 11/305,820; Mailing Date: Oct. 9, 2007, 8 pages.

Non-Final Office Action; U.S. Appl. No. 11/314,712; Mailing Date: Jan. 21, 2009, 8 pages.

Non-Final Office Action; U.S. Appl. No. 11/582,874; Mailing Date: Jan. 4, 2010, 9 pages.

Non-Final Office Action; U.S. Appl. No. 11/593,995; Mailing Date: Apr. 19, 2010, 10 pages.

Non-Final Office Action; U.S. Appl. No. 12/338,793; Mailing Date: Sep. 21, 2010, 9 pages.

Supplementary European Search Report; Application No. EP05849654.8; Applicant: Vertiflex, Inc; Date of Completion: May 15, 2009, 10 pages.

Supplementary European Search Report; Application No. EP07861721.4; Applicant: Vertiflex, Inc; Date of Completion: Nov. 24, 2009, 6 pages.

Supplementary European Search Report; Application No. EP09170304.1; Applicant: Vertiflex, Inc; Date of Completion: Nov. 11, 2009, 5 pages.

Supplementary European Search Report; Application No. EP09170338.9; Applicant: Vertiflex, Inc; Date of Completion: Nov. 12, 2009, 6 pages.

Swan, Colby, "Preliminary Design and Experimental Studies of a Novel Soft Implant for Correcting Sogittal P{lane Instability in the Lumbar Spine," Spine, 1997, 22(16), 1826-1827.

European Office Action Application No. EP05849654.8; Applicant: The Board of Trustees of the Leland Stanford Junior University; Date of Completion: Jun. 21, 2011, 4 pages.

Non-Final Office Action; U.S. Appl. No. 12/205,511 Mailing Date: Apr. 20, 2011, 9 pages.

Non-Final Office Action; U.S. Appl. No. 12/358,010 Mailing Date: Jul. 14, 2011; 9 pages.

Supplementary European Search Report; Application No. EP07861426.0; Applicant: Vertiflex, Inc; Date of Completion: Jun. 7, 2011, 6 pages.

Supplementary European Search Report; Application No. EP09702116.6; Applicant: Vertiflex, Inc; Date of Completion: Feb. 11, 2011, 6 pages.

Supplementary European Search Report; Application No. EP11151901.3; Applicant: Vertiflex, Inc; Date of Completion: Apr. 7, 2011, 6 pages.

* cited by examiner

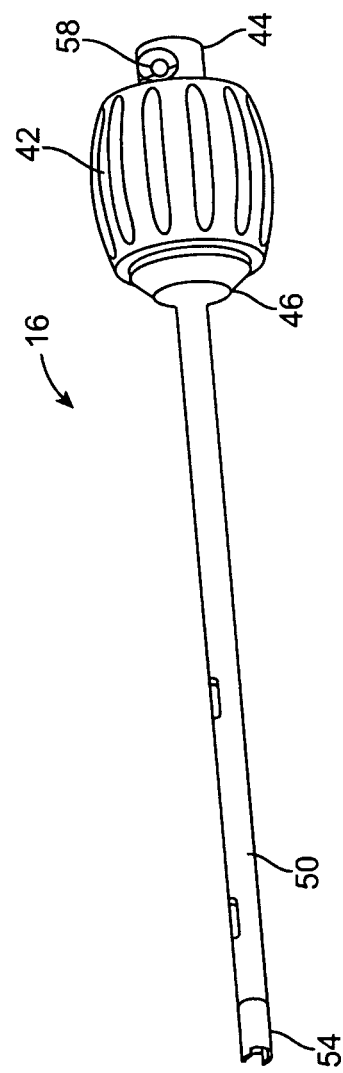

US 8,945,183 B2

INTERSPINOUS PROCESS SPACER INSTRUMENT SYSTEM WITH DEPLOYMENT INDICATOR

CROSS-REFERENCE TO RELATED APPLICATIONS

This application claims the benefit of and is a continuation-in-part of U.S. Provisional Patent Application Ser. No. 61/069,083 entitled "Spacer instrumentation system with deployment indicator" filed on Mar. 12, 2008 which is incorporated herein by reference in its entirety. This application also claims priority to and is a continuation-in-part of U.S. patent application Ser. No. 12/354,517 entitled "Interspinous spacer" filed on Jan. 15, 2009 which is a non-provisional of U.S. Provisional Patent Application No. 61/011,199 entitled "Interspinous spacer" filed on Jan. 15, 2008 both of which are incorporated by reference herein in their entireties. This application also claims priority to and is a continuation-in-part of U.S. patent application Ser. No. 12/338,793 entitled "Spacer insertion instrument" filed on Dec. 18, 2008, which issued as U.S. Pat. No. 8,613,747 on Dec. 18, 2008, which is a non-provisional of U.S. Provisional Patent Application Ser. No. 61/008,418 entitled "Spacer insertion instrument" filed on Dec. 19, 2007 both of which are incorporated herein by reference in their entireties. This application also claims priority to and is a continuation-in-part of U.S. patent application Ser. No. 12/205,511 entitled "Interspinous spacer" filed on Sep. 5, 2008, which issued as U.S. Pat. No. 8,123,782 on Feb. 28, 2012, which is a non-provisional of U.S. Provisional Patent Application Ser. No. 60/967,805 entitled "Interspinous spacer" filed on Sep. 7, 2007 and a continuation-in-part of U.S. patent application Ser. No. 12/220,427 entitled "Interspinous spacer" filed on Jul. 24, 2008, which issued as U.S. Pat. No. 8,277,488 on Oct. 2, 2012, which is a non-provisional of U.S. Provisional Patent Application Ser. No. 60/961,741 entitled "Interspinous spacer" filed on Jul. 24, 2007 and is a continuation-in-part of U.S. patent application Ser. No. 12/217,662 entitled "Interspinous spacer" filed on Jul. 8, 2008, which issued as U.S. Pat. No. 8,273,108 on Sep. 15, 2012, which is a non-provisional of U.S. Provisional Patent Application No. 60/958,876 entitled Interspinous spacer" filed on Jul. 9, 2007 and a continuation-in-part of U.S. patent application Ser. No. 12/148,104 entitled "Interspinous spacer" filed on Apr. 16, 2008, which issued as U.S. Pat. No. 8,292,922 on Oct. 23, 2012, which is a non-provisional of U.S. Provisional Patent Application Ser. No. 60/923,971 entitled "Interspinous spacer" filed on Apr. 17, 2007 and U.S. Provisional Patent Application Ser. No. 60/923,841 entitled "Spacer insertion instrument" filed on Apr. 16, 2007, all of which are hereby incorporated by reference in their entireties. This application is also a continuation-in-part of U.S. patent application Ser. No. 11/593,995 entitled "Systems and methods for posterior dynamic stabilization of the spine" filed on Nov. 7, 2006, which issued as U.S. Pat. No. 8,425,559 on Apr. 23, 2013, and a continuation-in-part of U.S. patent application Ser. No. 11/582,874 entitled "Minimally invasive tooling for delivery of interspinous spacer" filed Oct. 18, 2006, which issued as U.S. Pat. No. 8,128,662 on Mar. 6, 2012, and a continuation-in-part of U.S. patent application Ser. No. 11/314,712 entitled "Systems and methods for posterior dynamic stabilization of the spine" filed on Dec. 20, 2005, which issued as U.S. Pat. No. 8,152,837 on Apr. 10, 2012, and a continuation-in-part of U.S. patent application Ser. No. 11/190,496 entitled "Systems and methods for posterior dynamic stabilization of the spine" filed on Jul. 26, 2005, which issued as U.S. Pat. No. 8,409,282 on Apr. 2, 2013, and a continuation-in-part of U.S. patent application Ser. No. 11/079,006 entitled "Systems and methods for posterior dynamic stabilization of the spine" filed on Mar. 10, 2005, which issued as U.S. Pat. No. 8,012,207 on Sep. 6, 2011 and a continuation-in-part of U.S. patent application Ser. No. 11/052,002 entitled "Systems and methods for posterior dynamic stabilization of the spine" filed on Feb. 4, 2005, which issued as U.S. Pat. No. 8,317,864 on Nov. 27, 2012, and a continuation-in-part of U.S. patent application Ser. No. 11/006,502 entitled "Systems and methods for posterior dynamic stabilization of the spine" filed on Dec. 6, 2004, which issued as U.S. Pat. No. 8,123,807 on Feb. 28, 2012, and is a continuation-in-part of U.S. patent application Ser. No. 10/970,843 entitled "Systems and methods for posterior dynamic stabilization of the spine" filed on Oct. 20, 2004, which issued U.S. Pat. No. 8,167,944 on May 1, 2012, and a continuation-in-part of U.S. patent application Ser. No. 11/006,521 entitled "Systems and methods for stabilizing the motion or adjusting the position of the spine" filed on Dec. 6, 2004, and is a continuation-in-part of U.S. patent application Ser. No. 11/305,820 entitled "Systems and methods for posterior dynamic stabilization of the spine" filed on Dec. 15, 2005, which issued as U.S. Pat. No. 7,763,074 on Jul. 27, 2010, all of which are hereby incorporated by reference in their entireties.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down—all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent spinous processes of a patient's spine. The implanted spacer opens the spinal canal, neural foramen, maintains the desired distance between vertebral body segments, and as a result, reduces the impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous spacers and instruments that are used to implant them that work well with surgical techniques that are percutaneous and/or minimally invasive for the patient that can also be used in an open or mini-open procedure. The present invention sets forth such an instrument system.

SUMMARY

According to one aspect of the invention, an instrument system is provided. The system includes an interspinous process spacer, an inserter, a driver and a deployment indicator. The inserter is configured to releasably attach to the spacer at one end for implanting the spacer into a patient's interspinous process space. The driver that is connected to the inserter is configured to arrange the spacer from at least one undeployed configuration to at least one deployed configuration and the deployment indicator provides at least one information to the user pertaining to the degree of deployment of the attached spacer.

According to another aspect of the invention, an instrument for inserting a deployable interspinous process spacer into a patient is provided. The instrument includes a first end connectable to an interspinous process spacer and a second end configured to arrange a connected spacer between at least a first configuration and at least a second configuration. The instrument includes a sensor configured to measure the arrangement of a connected spacer and provide a signal regarding the arrangement of a connected spacer to the user.

BRIEF DESCRIPTION OF THE DRAWINGS

FIG. 3A illustrates a perspective view of a driver according to the present invention.

DETAILED DESCRIPTION

Figure 1A:
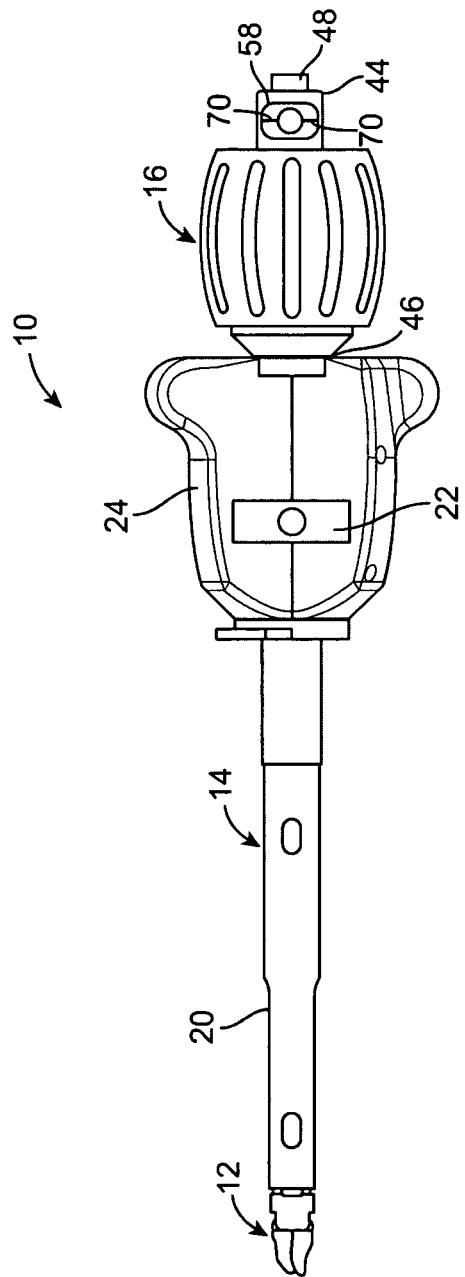
FIG. 1A illustrates a side view of a spacer instrument system connected to a spacer in a closed or an undeployed configuration according to the present invention.
Figure 1B:
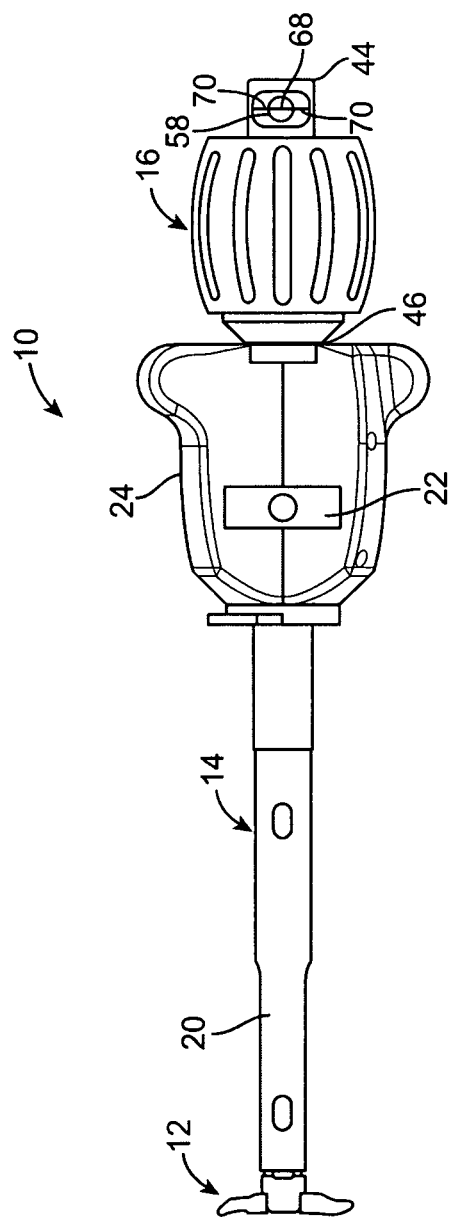
FIG. 1B illustrates a side view of a spacer instrument system connected to a spacer in an open or deployed configuration according to the present invention.

Referring first to FIGS. 1A and 1B, there is shown a spacer instrument system 10 with a deployment indicator according to the present invention connected to an interspinous process spacer 12 in a closed or undeployed configuration and in an open or deployed configuration, respectively. The spacer instrument system 10 includes an inserter 14 and a driver 16.

Still referencing FIGS. 1A and 1B and with additional reference to FIG. 2, the inserter 14 will now be described. The inserter 14 is of the type described in co-pending U.S. patent application Ser. No. 12/338,793 entitled "Spacer insertion instrument" filed on Dec. 18, 2008 which claims the benefit of U.S. Provisional patent application Ser. No. 61/008,418 entitled "Spacer insertion instrument" filed on Dec. 19, 2007 both of which are assigned to VertiFlex, Inc. and hereby incorporated by reference in their entireties. The inserter 14 is configured to releasably clamp to a body of an interspinous process implant or spacer 12 to be delivered into or removed from a patient using the system 10. The inserter 14 includes an inner shaft 18, an outer shaft 20, a control 22 and handle assembly 24. The inner shaft 18 is connected to the handle assembly 24 of the inserter 14 and the outer shaft 20 is passed over the inner shaft 18 and allowed to translate with respect to the inner shaft 18 by means of a control 22 that is threadingly engaged with the outer shaft 20. With rotation of the control 22 in one direction, the outer shaft 20 translates distally with respect to the stationary inner shaft 18. With rotation of the control 22 in the opposite direction, the outer shaft 20 translates proximally with respect to the stationary inner shaft 18. In another variation of the invention, the outer shaft 20 is connected to handle assembly 24 and the inner shaft is threadingly connected to the control 22 such that rotation of the control 22 moves the inner shaft 18 with respect to the outer shaft 20 proximally or distally. Although rotation of the control 22 is used in one variation, other variations are within the scope of the present invention such as, for example, translation of the control 22 or movement of the outer shaft 20 relative to the inner shaft 18.

Figure 2:
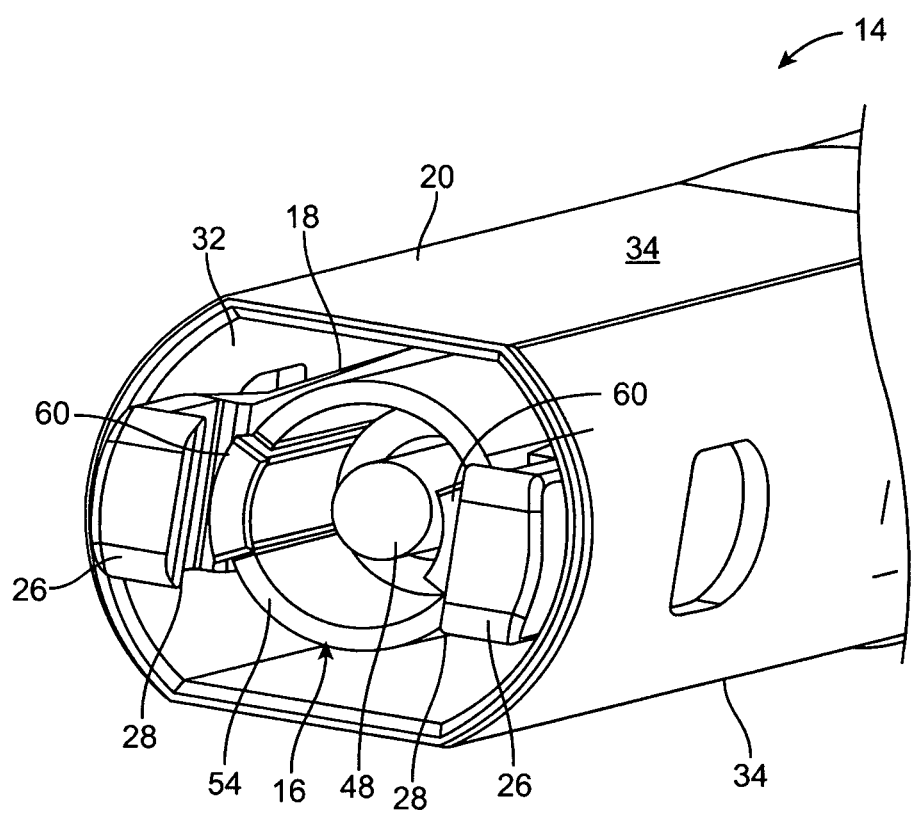
FIG. 2 illustrates a perspective partial end view of an inserter and driver of a spacer instrument system according to the present invention.

With particular reference to FIG. 2, the inner shaft 18 of the inserter 14 is substantially cylindrical in shape having a central bore extending from end to end. The distal end of the inner shaft 18 includes a pair of prongs 26 with each prong being substantially oppositely located from each other. The finger-like prongs 26 are flexible and, when in a normal position, splay slightly outwardly from the longitudinal axis. The prongs 26 are configured to connect with the spacer 12. In particular, the prongs 26 include extensions 28 that extend inwardly toward the longitudinal axis in a hook-like fashion. These extensions 28 are configured to be inserted into prong-receiving portions 30 (see FIGS. 4A, 4B and 4C) on the spacer 12 and securely clamp thereto. The prongs 26 also include conforming surfaces configured to conform to the spacer 12 in a manner best suited for secure attachment thereto. The proximal end of the inner shaft 18 is configured for insertion into and connection with a conformingly shaped recess in the handle 24.

The outer shaft 20 of the inserter 14 will now be described. As seen in FIG. 2, the outer shaft 22 is substantially cylindrical in shape having a central bore 32 extending from end to end. The outer shaft 20 is sized such that the inner shaft 18 fits inside the outer shaft 20. The distal end includes a pair of flattened portions 34 located substantially opposite from each other for a narrower profile and in one variation a ramped profile for insertion or placement between adjacent spinous processes of a patient's spine. The ramped profile serves to distract the adjacent spinous processes apart slightly as the inserter is being inserted between the adjacent spinous processes for insertion of the connected spacer 12 wherein the flattened portions 34 are separated by an increasingly wider distance towards the proximal end of the instrument. The outer shaft 20 includes a threaded proximal portion (not shown). The threaded proximal portion is configured for threaded connection with the control 22 such that movement of the control 22 moves the outer shaft 20.

The control 22 includes a user interface such as a finger portion or grip. In one variation, the user interface is an outer circular or disk-shaped portion for easily effecting rotation of the control 22 with a thumb or index finger. The control 22 is configured to effect relative translation of the inner shaft 18 with respect to the outer shaft 20.

Figure 4A:
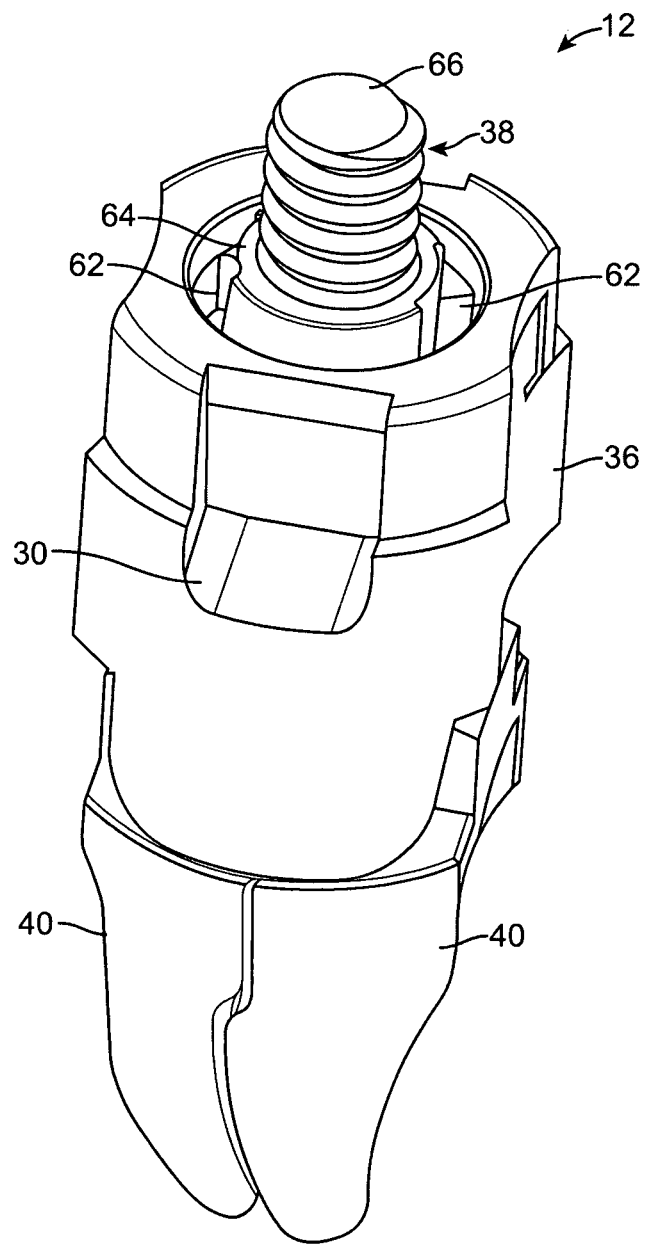
FIG. 4A illustrates a perspective view of a spacer in an undeployed or closed configuration according to the present invention.
Figure 4B:
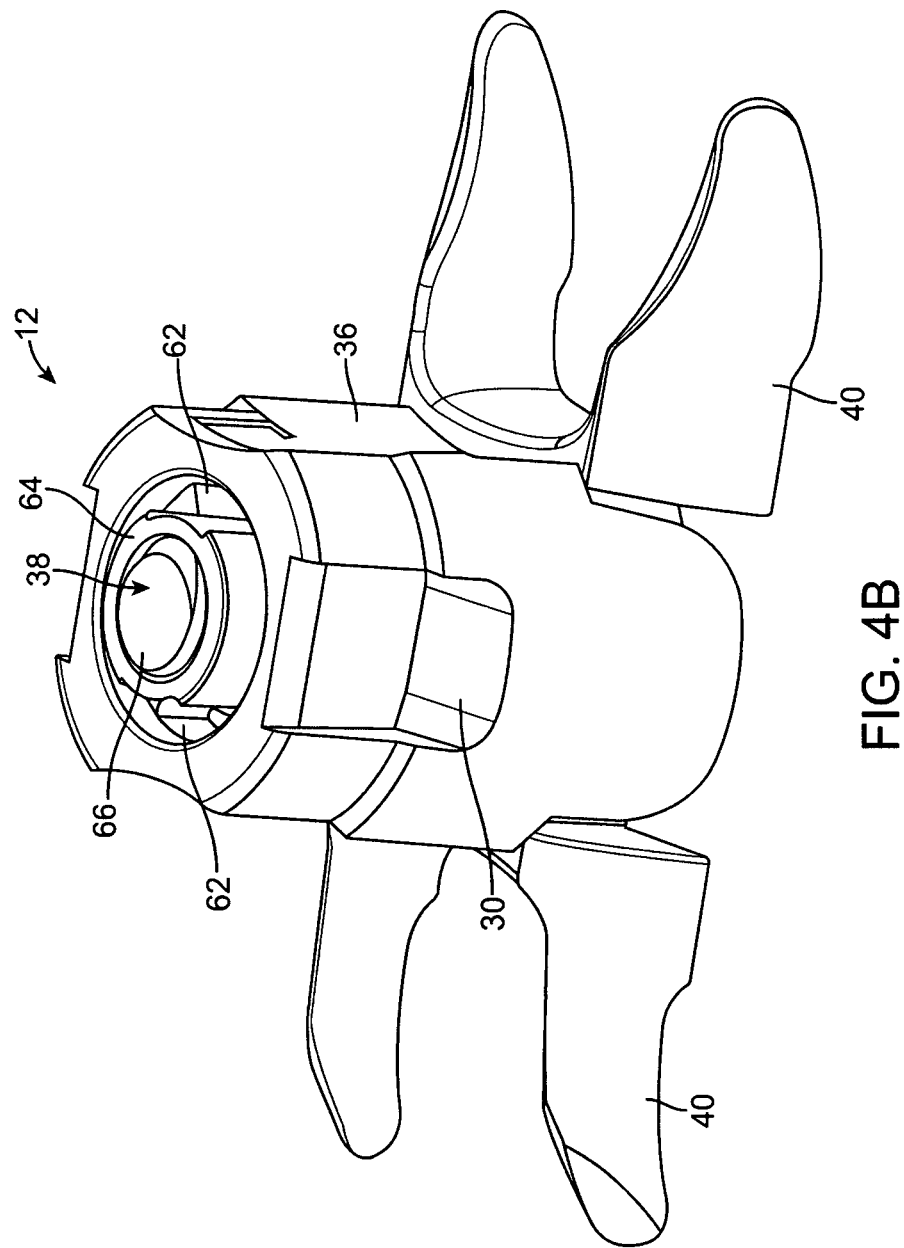
FIG. 4B illustrates a perspective view of a spacer in a deployed or open configuration according to the present invention.
Figure 4C:
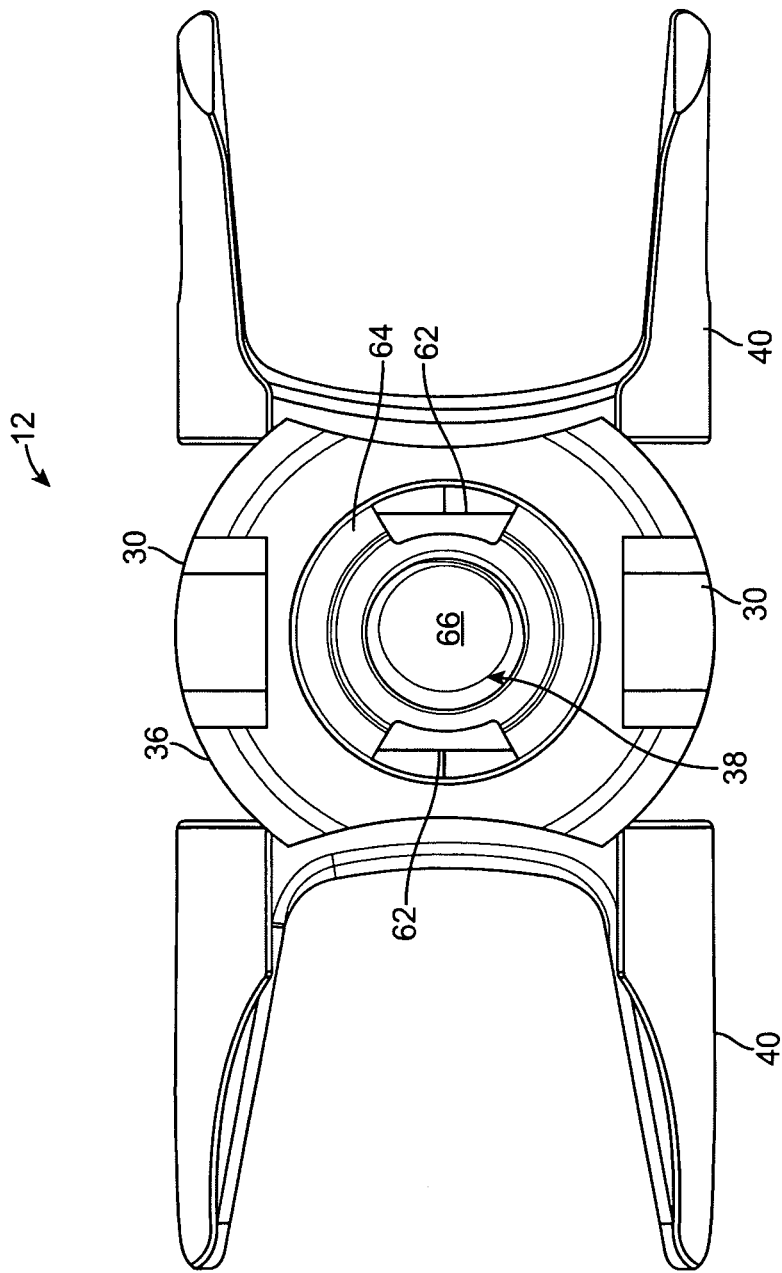
FIG. 4C illustrates a top view of a spacer in a deployed or open configuration according to the present invention.

The spacer instrument system 10 functions to engage with, insert and deploy an interspinous spacer 12 in an interspinous process space between two adjacent vertebrae. Illustrative examples of interspinous spacers that are compatible with the insertion instrument are described in applicant's co-pending U.S. patent application Ser. No. 12/148,104 entitled "Interspinous spacer" filed on Apr. 16, 2008 which claims the benefit of U.S. Provisional Patent Application Ser. No. 60/923,841 entitled "Spacer insertion instrument" filed on Apr. 16, 2007 and U.S. Provisional Patent Application Ser. No. 60/923,971 entitled "Interspinous spacer" filed on Apr. 17, 2007, U.S. patent application Ser. No. 12/217,662 entitled "Interspinous spacer" filed on Jul. 8, 2008 which claims the benefit of U.S. Provisional Patent Application Ser. No. 60/958,876 entitled "Interspinous spacer" filed on Jul. 9, 2007, U.S. patent application Ser. No. 12/220,427 entitled "Interspinous spacer" filed on Jul. 24, 2008 which claims the benefit of U.S. Provisional Patent Application Ser. No. 60/961,741 entitled "Interspinous spacer" filed on Jul. 24, 2007, and U.S. patent application Ser. No. 12/205,511 entitled "Interspinous spacer" filed on Sep. 5, 2008 which claims the benefit of U.S. Provisional Patent Application Ser. No. 60/967,805 entitled "Interspinous spacer" filed on Sep. 7, 2007, and U.S. patent application Ser. No. 12/354,517 entitled "Interspinous spacer" filed on Jan. 15, 2009 which claims the benefit of U.S. Provisional Patent Application Ser. No. 61/011,199 entitled "Interspinous spacer" filed on Jan. 15, 2008 the disclosure of all of which are incorporated herein by reference in their entireties. An example of an interspinous spacer 12 is shown in FIGS. 4A, 4B and 4C. In general, each spacer 12 includes a body portion 36 with at least one prong receiving portion 30 for connecting with the instrument 10, at least one wing 40 rotatably connected to the body 36 and an actuator shaft 38 housed in the body portion 36 and configured to arrange the at least one wing 40 from at least one undeployed configuration (see FIG. 4A) to at least one deployed configuration (see FIGS. 4B and 4C) and vice versa. The wings 40 are configured to laterally stabilize the body portion 36 relative to thespinous processes, seat and/or space apart the spinous processes of adjacent vertebrae when in the deployed configuration to relieve pain.

The spacer instrument system 10 utilizes the working channel that is preferably created by the use of one or more tools such as a target needle, K-wire, dilators, mounting bracket, cannula, stabilizing arm, interspinous knife, interspinous reamer, and interspinous gage, all described in applicant's co-pending U.S. patent application Ser. No. 11/582,874 entitled "Minimally invasive tooling for delivery of interspinous spacer" filed on Oct. 18, 2006, incorporated herein by reference in its entirety. The inserter 14 is typically inserted through a cannula with the distal end positioned at the interspinous process space in a minimally invasive, percutaneous, mini-open or open surgical procedure. In some procedures, a cannula is not employed to deliver the spacer instrument system 10 and spacer 12 to the interspinous space.

In use, a spacer 12 is placed in juxtaposition to the distal end of the inserter 14 such that the prongs 26 of the inserter 14 are adjacent to the prong receiving portions 30 on the spacer 12. The control 22 is then activated to clamp the prongs 26 of the inner shaft 18 onto the spacer 12. In particular, the control 22 is rotated in one direction which advances the outer shaft 20 over the inner shaft 18 to thereby inwardly deflect the outwardly splayed prongs 26 at the distal end of the inner shaft 18. This inward deflection allows the prongs 26 to engage the spacer body 36 and, in particular, allows the prong extensions 28 to be inserted into the prong receiving portions 30 and with further rotation of the control 22 to lock the inserter 14 securely onto the spacer 12. Reverse rotation of the control 22 translates the outer shaft 20 proximally to expose the prongs 26 allowing them to splay outwardly to their pre-stressed normal position and thereby release the spacer 12 from the inserter 14.

If a cannula is employed in the operative site, the inserter 14 with the attached spacer 12 is sized to fit through a cannula and is passed through the cannula to the interspinous process space. Once in position inside the patient, the driver 16 is inserted into the proximal opening of the central passageway of the inserter 14 and passed until the driver 16 connects with the spacer 12.

Turning now to FIGS. 3A, 3B, 3C and 3D, the driver 16 will now be described. The driver 16 includes: (1) a handle 42 having a proximal end 44 and a distal end 46, (2) a inner shaft 48, (3) outer shaft 50, (3) a spacer engaging bit 54 connected to the distal end of the outer shaft 50, and (4) a spring 52. The outer shaft 50 which is connected to the distal end 46 of the handle 42 includes a lumen in which the inner shaft 48 is disposed. The inner shaft 48 includes a collar 56 (shown in FIG. 3C) configured to be located inside the handle 42 and biased against the spring 52 and configured such that the spring 52 forces the inner shaft 48 distally in a direction towards the spacer engaging bit 54. The proximal end 44 of the handle 42 includes a deployment indicator window 58 through which the inner shaft 48 is viewed. FIG. 2 illustrates the distal end of the driver 16 inserted into the inserter 14.

Depending on the spacer 12 design, the connection of the driver 16 with the spacer 12, in particular the spacer engaging bit 54, will be different. In general, however, the driver 16 connects to the spacer 12 such that movement, such as rotation, of the driver 16 effects deployment of a deployable spacer 12, in particular, the deployment of the at least one wing 40 of the spacer 12. In particular, and with respect to the spacer embodiment shown in FIGS. 4A-4C, rotation of the driver 16 that is connected to the spacer 12 effects translation of the actuator shaft 38 of the spacer 12 which in turn is connected to the at least one wing 40 causing it to deploy into an expanded configuration or deployed configuration.

The driver 16 that is configured to connect with the spacer 12 of FIGS. 4A-4C will have a spacer engaging bit 54 that includes two projecting features 60. The two projecting features 60 engage complementary features 62 on the spacer 12 located inside the spacer body portion 36 as shown in FIGS. 4A-4C. Once engaged to the spacer 12, rotation of the driver 16 rotates the spindle 64 which in turn advances the actuator shaft 38 to deploy the wings 70 into the configuration shown in FIGS. 4B and 4C. Reverse rotation of the driver 16 will turn the spindle 64 in an opposite direction and proximally translate the actuator shaft 38 to undeploy the wings 40. As can be seen in FIGS. 4B and 4C, when in the deployed configuration, the actuator shaft 38 is distally translated with rotation of the driver 16 relative to when in the undeployed configuration as shown in FIG. 4A wherein the actuator shaft 38 projects proximally from the spacer body 36. This distance traveled by the actuator shaft 38 provides the information about the degree of deployment of the wings 40 of the spacer 12 that is communicated to the inner shaft 48 of the driver 16. With the inserter 14 connected to the spacer 12 and the driver 16 inserted into the central passageway of the inserter 14 and connected to the spindle 64 such that the projecting features 60 of the bit 54 engage the features 62 on the spindle 64, the inner shaft 48 of the driver 16 contacts the proximal end 66 of the actuator shaft 38 and will bias the inner shaft 48 a distance related to the distance with which the actuator shaft 38 projects proximally from the spacer body 36. Hence, as the driver 16 is rotated to effect translation of the actuator shaft 38 inwardly or outwardly to deploy or undeploy the spacer, the bias force of the spring 52 will keep the distal end of the inner shaft 48 of the driver 16 in contact with the proximal end 66 of the actuator shaft 38 as it translates proximally or distally providing an indication as to the degree of deployment of the spacer 12. The indication as to the degree of deployment of the spacer 12 is viewed at the proximal end of the system 10.

Because the handle 24 resides outside the patient, the deployment information is readily visible to the surgeon.

Referring back to FIG. 1A, there is shown the system 10 in an undeployed configuration. As can be seen, at the proximal end, the inner shaft 48 projects outwardly from the proximal end 44 of the handle 24. As the driver 16 is rotated to deploy the spacer 12, the inner shaft 48 moves distally until the inner shaft 48 does not project outwardly from the proximal end 44 of the handle 24 and/or is co-planar with the proximal end 44 of the handle 24 as shown in FIG. 1B, thereby providing the user with a visual indication of the degree of deployment of the spacer 12 wherein if the inner shaft 48 is not projecting then the spacer 12 is fully deployed and if the inner shaft 48 is projecting from the proximal end 44 of the handle 24 then a state other than full deployment is indicated. The degree of deployment is related to the distance with which the inner shaft 48 is projecting outwardly from the proximal end 44 of the handle 24. The proximal end of the inner shaft 48 or "button" provides the surgeon not only with visual feedback but also tactile feedback as to the degree of deployment.

Figure 3B:
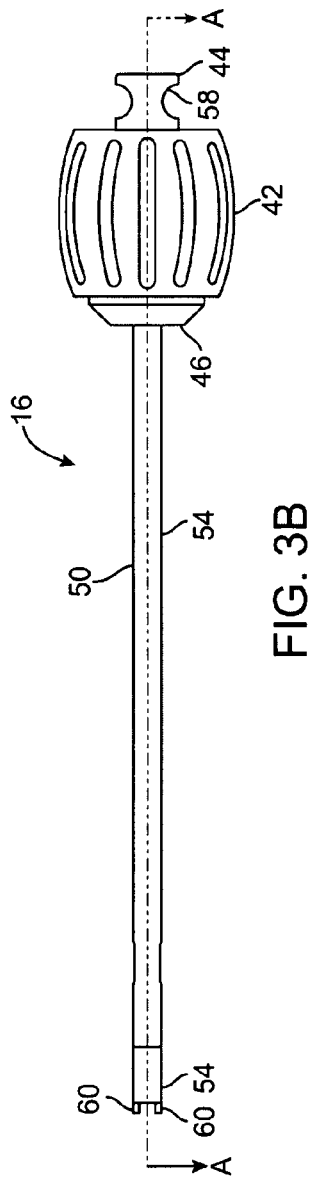
FIG. 3B illustrates a side view of a driver according to the present invention.
Figure 3C:
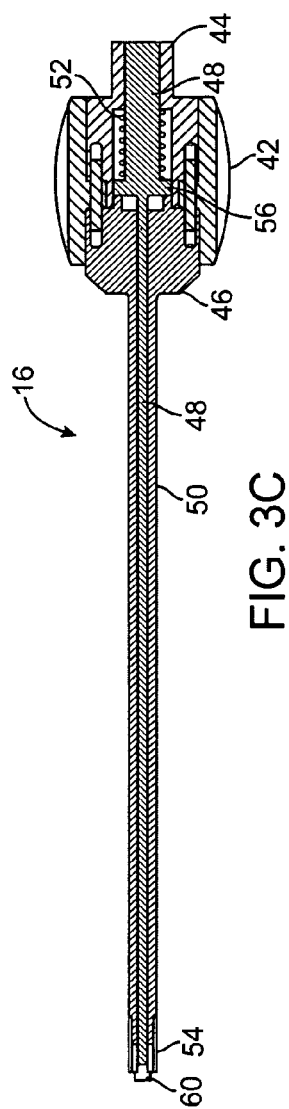
FIG. 3C illustrates a cross-sectional view taken along line A-A of FIG. 3B of the driver according to the present invention.
Figure 3D:
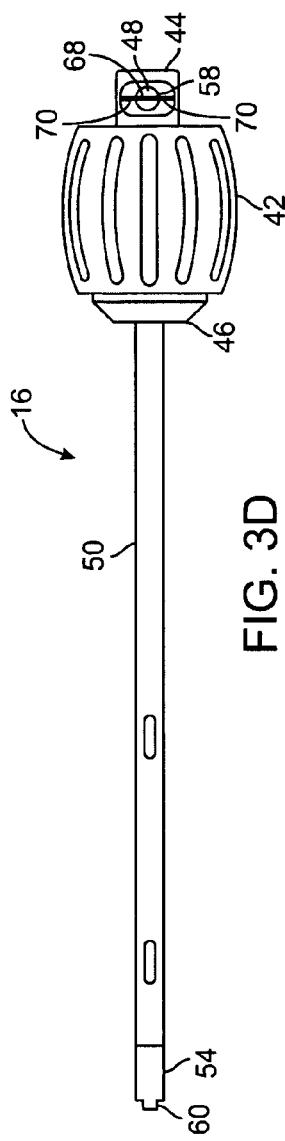
FIG. 3D illustrates a side view of a driver according to the present invention.

Another deployment indicator is provided alternatively or in conjunction with the projection of the inner shaft 48 from the proximal end 44 just described. This other deployment indicator includes an indicator line 68 (shown in FIGS. 1B and 3D) provided on the inner shaft 48 of the driver 16, which becomes visible through the indicator window 58 as the inner shaft 48 translates with deployment of the spacer 12. When in the undeployed configuration as shown in FIG. 1A, the indicator line 68 is proximal of the window 58 and therefore not visible through the indicator window 58. When the spacer 12 approaches a deployed configuration, the indicator line 68 will enter the indicator window 58 and be visible to the user. An additional alignment line or lines 70 is provided on the proximal end 44 of the handle 24 adjacent to the indicator window 58 as shown in FIGS. 1B and 3D. When the indicator line 68 on the inner shaft 48 is aligned with the alignment line or lines 70 on the handle 24, a fully deployed configuration of the spacer 12 is indicated providing a visual information of deployment to the surgeon.

The above description is one variation of mechanical sensor connected to the instrument for measuring the arrangement of a connected spacer 10. One skilled in the art will recognize that the instrument can be configured with any suitable sensor that can be effectively employed to measure the arrangement of the spacer and provide a signal to the user regarding the arrangement of the connected spacer. Examples of suitable sensors include, but are not limited to mechanical, position, optical, electromagnetic, motion, and distance sensors. Of course, suitable signals communicating the measured information include audible, visual, tactile signals and the like. The signal may be transmitted to a receiver located on the instrument itself preferable at a location that is resident outside the patient while in use or at a location remote of the instrument. In one variation, the sensor provides a signal only upon full deployment of the spacer. In another variation, the sensor provides continuous information as to the arrangment of the spacer.

Hence, the present invention advantageously provides information regarding the degree of deployment of the spacer to the surgeon which is particularly advantageous in minimally invasive and percutaneous procedures where the device cannot be viewed without the aid of fluoroscopy because of visual obstruction accompanying very small incisions. As a result of the deployment information provided by the system, this invention advantageously reduces time required to implant the spacer and also advantageously reduces the number of fluoroscopy shots that the clinicians and patients are exposed to during the procedure as the deployment information is readily provided to the surgeon by the spacer instrument system with deployment indicator that is located outside patient incision.

All publications mentioned herein are incorporated herein by reference to disclose and describe the methods and/or materials in connection with which the publications are cited. The preceding illustrates the principles of the invention. It will be appreciated that those skilled in the art will be able to devise various arrangements which, although not explicitly described or shown herein, embody the principles of the invention and are included within its spirit and scope.

We claim:

1. An instrument system comprising:
   a spacer configured to be arranged from at least one undeployed configuration to at least one deployed configuration;
   an inserter connectable to the spacer;
   a driver configured to arrange the spacer from the at least one undeployed configuration to the at least one deployed configuration; and
   a deployment indicator including a spring loaded shaft biased against a movable portion of the spacer at one end; wherein movement of the movable portion of the spacer moves the shaft; said movement of said shaft being visible at a second end to provide at least one information pertaining to a degree of deployment of the spacer.

2. The instrument system of claim 1 wherein the driver is insertable into a passageway of the inserter and configured at one end to engage the spacer when the spacer is connected to the inserter.

3. The instrument system of claim 1 wherein at least a portion of the deployment indicator is configured to be resident outside a patient.

4. The instrument system of claim 1 wherein when one end of the inserter is connected to the spacer and said end is inserted into a patient, the instrument is configured such that the deployment indicator is resident outside the patient.

5. The instrument system of claim 1 wherein the deployment indicator is connectable to the spacer.

6. The instrument system of claim 1 wherein the shaft includes an indicator line that is configured to indicate at least one deployed configuration of the spacer.

7. The instrument system of claim 6 wherein the indicator line is configured to be visible through a window; the system further including at least one alignment line adjacent to said window and configured such that alignment of the indicator line with the alignment line indicates a fully deployed configuration of the spacer.

8. The instrument system of claim 1 wherein the shaft has a first position to indicate a first deployment information and has a second position to indicate a second deployment information.

9. The instrument system of claim 8 wherein the first position is characterized by the shaft projecting at the second end and the second position characterized by the shaft being substantially flush with respect to at least one surface.

10. The instrument system of claim 1 wherein the deployment indicator provides a visual indication of the configuration of the spacer as the spacer moves from the at least one undeployed configuration to the at least one deployed configuration.

11. The instrument system of claim 1 wherein the spacer includes a first wing and a second wing, the first wing is movable between a first undeployed position and a first deployed position, the second wing is movable between a second undeployed position and a second deployed position, and wherein the deployment indicator informs the operator of both a position of the first wing as the first wing moves between the first undeployed position and the first deployed position and a position of the second wing as the second wing moves between the second undeployed position and the second deployed position.

12. The instrument system of claim 1 wherein the spacer includes a first wing and a second wing, the first wing and the second wing are movable between an undeployed position and a spinous process received position, and wherein the deployment indicator provides a visual indication of a position of the first wing and a position of the second wing as the first wing and the second wing move from the undeployed position to the spinous process received position.

13. The instrument system of claim 1 wherein
the spacer includes a body portion, a first wing configured to receive a first spinous process, and a second wing configured to receive a second spinous process; and
the deployment indicator is configured to inform the operator of an amount of rotation of at least one of the first and second wings when the driver causes the first wing to rotate relative to the body portion to receive the first spinous process and causes the second wing to rotate relative to the body portion to receive the second spinous process.

14. An instrument system comprising:
a spacer having engaging portions movable between an undeployed position and a deployed position;
an inserter releasably coupled to the spacer, the inserter having a central bore extending therethrough;
a driver having a first end portion opposite a second end portion, wherein the first end portion is movably positioned within at least a section of the central bore of the inserter and includes projections that contact corresponding engaging portions of the spacer to move the engaging portions from the undeployed position to the deployed position in response to movement of the second end portion; and
a deployment indicator including a spring loaded shaft biased against a movable portion of the spacer at one end, wherein movement of the movable portion of the spacer moves the shaft, wherein movement of the shaft is visible at a second end to provide at least one information pertaining to the degree of deployment of the spacer.

15. The instrument system of claim 14 wherein deployment indicator is a first deployment indicator, and wherein the instrument system further includes a second deployment indicator that provides a second visual indication of the positions of the engaging portions of the spacer, the central bore of the inserter is a first central bore, and wherein the driver includes a second central bore extending therethrough, and wherein the spring loaded shaft extends through at least a portion of the second central bore.

16. The instrument system of claim 14 wherein the shaft is biased towards the spacer and includes a first end portion opposite a second end portion, wherein the first end portion of the shaft contacts the spacer and a position of the second end portion of the shaft relative to the second end portion of the driver provides the visual indication of the positions of the engaging portions of the spacer.

17. The instrument system of claim 14, further comprising:
an indicator window;
an alignment line adjacent to the window; and
an indicator line movable with the driver, wherein when the indicator line is at least generally aligned with the alignment line the engaging portions of the spacer are in the deployed position.

18. The instrument system of claim 14 wherein the spacer includes a first wing and a second wing, the first wing is movable between a first undeployed position and a first deployed position, the second wing is movable between a second undeployed position and a second deployed position, and wherein the deployment indicator visually informs an operator of both a position of the first wing moving between the first undeployed position and the first deployed position and a position of the second wing moving between the second undeployed position and the second deployed position.

19. The instrument system of claim 14 wherein the spacer includes a first wing configured to receive a first spinous process and a second wing configured to receive a second spinous process, and wherein the deployment indicator is configured to inform the operator of both a position of the first wing when the driver mechanically moves the first wing between a first undeployed position and a first deployed position and a position of the second wing when the driver mechanically moves the second wing between a second undeployed position and a second deployed position.

20. The instrument system of claim 14 wherein the deployment indicator informs the operator of the position of at least one wing of the spacer independent of physical contact between the at least one wing and the subject's body.

* * * * *

UNITED STATES PATENT AND TRADEMARK OFFICE
CERTIFICATE OF CORRECTION

| | | |
|---|---|---|
| PATENT NO. | : 8,945,183 B2 | Page 1 of 1 |
| APPLICATION NO. | : 12/400601 | |
| DATED | : February 3, 2015 | |
| INVENTOR(S) | : Moti Altarac et al. | |

It is certified that error appears in the above-identified patent and that said Letters Patent is hereby corrected as shown below:

On the title page, item (63), in column 1, under "Related U.S. Application Data", line 2, delete "which is" and insert -- and --, therefor.

On title page 3, in column 2, References Cited under "U.S. Patent Documents", line 6, delete "Amin" and
insert -- Arnin --, therefor.

On title page 6, in column 2, References Cited under "Other Publications", line 50, delete "Sogittal P{lane" and insert -- Sagittal Plane --, therefor.

In the Specification

In column 1, line 42, delete "Interspinous" and insert -- "Interspinous --, therefor.

In column 1, line 58, after "filed" insert -- on --.

In column 5, line 31, delete "thespinous" and insert -- the spinous --, therefor.

In column 7, line 56, delete "arrangment" and insert -- arrangement --, therefor.

Signed and Sealed this
Twenty-second Day of September, 2015

Michelle K. Lee
*Director of the United States Patent and Trademark Office*